United States Patent
Linde, II

(10) Patent No.: US 6,342,497 B1
(45) Date of Patent: Jan. 29, 2002

(54) 2"-DEOXY HYGROMYCIN DERIVATIVES

(75) Inventor: Robert Gerald Linde, II, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/380,718

(22) PCT Filed: Apr. 8, 1999

(86) PCT No.: PCT/IB99/00611

§ 371 Date: Sep. 7, 1999

§ 102(e) Date: Sep. 7, 1999

(87) PCT Pub. No.: WO99/57127

PCT Pub. Date: Nov. 11, 1999

Related U.S. Application Data

(60) Provisional application No. 60/084,058, filed on May 4, 1998.

(51) Int. Cl.$^7$ .................... A61K 31/36; A61K 31/4409; C07D 317/46; C07D 405/10; C07D 405/14
(52) U.S. Cl. .................... 514/233.8; 514/338; 514/465; 544/109; 546/283.7; 549/435
(58) Field of Search .............................. 514/233.8, 338, 514/465; 544/109; 546/283.7; 549/435

(56) References Cited

FOREIGN PATENT DOCUMENTS

JP        01-316393 A  *  3/1990

OTHER PUBLICATIONS

Hecker et al. Bioorg. Med. Chem. Lett. vol. 2 pp. 1043–1046, 1992.*
Hecker et al. Bioorg. Med. Chem. Lett. vol. 2 pp. 1015–1018, 1992.*
Jaynes et al. Bioorg. Med. Chem. Lett. vol. 3 (8) 1993 pp. 1531–1536.*

* cited by examiner

*Primary Examiner*—Taofiq A. Solola
(74) *Attorney, Agent, or Firm*—Peter C. Richardson; Paul H. Ginsburg; Israel Nissenbaum

(57) ABSTRACT

This invention relates to compounds of the formula

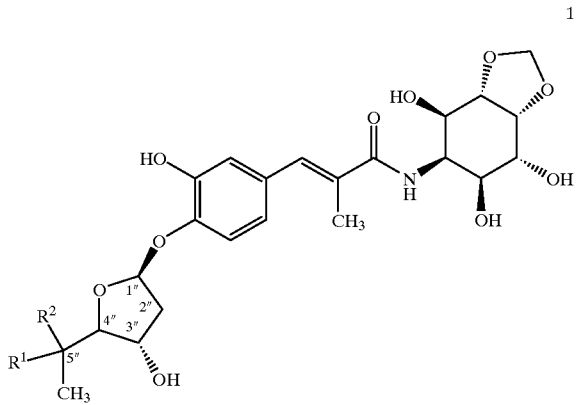

and to pharmaceutically acceptable salts, prodrugs and solvates thereof, wherein $R^1$ and $R^2$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

13 Claims, No Drawings

2"-DEOXY HYGROMYCIN DERIVATIVES

This is a 371 of PCT/IB99/100611 filed Apr. 8, 1999 which claims the benefit of Prov. application No. 60/084,058 filed May 4, 1998.

BACKGROUND OF THE INVENTION

This invention relates to novel 2"-deoxy hygromycin A derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

The compounds of the present invention may be derived from hygromycin A. Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina* (Treponema) *hyodysentenae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5' alcohol is referred to in R. L. Mann and D. O. Woolf, ibid., as well as in S. J. Hecker et al., *Bioorg. Med. Chem. Lett.* 1992, 2, 533 and S. J. Hecker et al., *Bioorg. Med. Chem. Lett.* 1993, 3, 295; furanose analogues are referred to in B. H. Jaynes et al., *Bioorg. Med. Chem Lett.* 1993, 3, 1531, and B. H. Jaynes et al., *J. Antibiot.* 1992, 45, 1705; aromatic ring analogues are referred to in S. J. Hecker et al., *Bioorg. Med. Chem. Lett.* 1993, 3, 289, and C. B. Cooper et al., *Bioorg. Med. Chem. Lett.* 1997, 7, 1747; enamide analogues are referred to in S. J. Hecker et al., *Bioorg. Med. Chem. Lett.* 1992, 2, 533; aminocyclitol analogues are referred to in S. J. Hecker et al., *Bioorg. Med. Chem. Lett.* 1992, 2, 1015, and in S. J. Hecker et al., *Bioorg. Med. Chem. Lett.* 1992, 2, 1043. The hygromycin derivatives of the present invention possess activity against both gram-negative and gram-positive bacteria and protozoa.

United States provisional patent application No. 60/084058, filed May 4, 1998, entitled "Hygromycin A Derivatives", (No. 60/084,058), with named inventors K. E. Brighty, R. G. Linde II, M. R. Jefson, E. L. McCormick and S. S. Guhan, also refers to hygromycin A analogues and is incorporated herein by reference in its entirety.

SUMMARY OF THE INVENTION

The present invention relates to compounds of the formula

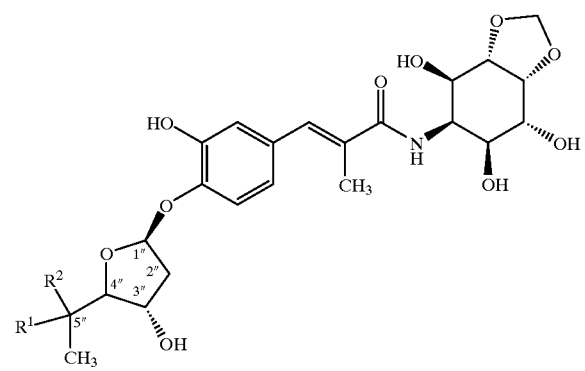

and to pharmaceutically acceptable salts, prodrugs and solvates thereof wherein:

$R^1$ is H and $R^2$ is —$NR^3R^4$, —$NR^4C(O)R^3$, —$OC(O)NR^3R^4$ or —$OR^3$;

or $R^1$ and $R^2$ are taken together to form =O, =N—$OR^3$, =$CR^4R^3$, =$CR^4C(O)R^3$, =$CR^4C(O)OR^3$, or =$CR^4C(O)NR^3R^4$;

each $R^3$ is independently selected from H, $C_1$–$C_{10}$ alkyl, $C_2$–$C_{10}$ alkenyl, —$(CH_2)_t(C_3$–$C_{10}$ cycloalkyl), —$(CH_2)_t(C_6$–$C_{10}$ aryl), and —$(CH_2)_t$(4–10 membered heterocyclic), wherein t is an integer ranging from 0 to 5, said alkyl group optionally contains 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^3$ groups are optionally fused to a benzene ring, a $C_5$–$C_8$ saturated cyclic group, or a 4–10 membered heterocyclic group; the —$(CH_2)_t$— moieties of the foregoing $R^3$ groups optionally include a carbon-carbon double or triple bond where t is an integer between 2 and 5; and the foregoing $R^3$ groups, except H but including any optional fused rings referred to above, are optionally substituted by 1 to 5 $R^5$ groups;

each $R^4$ is independently H or $C_1$–$C_{10}$ alkyl;

each $R^5$ is independently selected from $C_1$–$C_{10}$ alkyl, $C_3$–$C_{10}$ cycloalkyl, halo, cyano, nitro, trifluoromethyl, diifluoromethoxy, trifluoromethoxy, azido, —$OR^6$, —$C(O)R^6$, —$C(O)OR^6$, —$NR^7C(O)OR^9$, —$OC(O)R^6$, —$NR^7SO_2R^9$, —$SO_2NR^6R^7$, —$NR^7C(O)R^6$, —$C(O)NR^6R^7$, —$NR^6R^7$, —$S(O)_j(CH_2)_m(C_6$–$C_{10}$ aryl), —$S(O)_j(C_1$–$C_6$ alkyl), wherein j is an integer from 0 to 2, —$(CH_2)_m(C_6$–$C_{10}$ aryl), —$O(CH_2)_m(C_6$–$C_{10}$ aryl), —$NR^7(CH_2)_m(C_6$–$C_{10}$ aryl), and —$(CH_2)_m$(4–10 membered heterocyclic), wherein m is an integer ranging from 0 to 4; said alkyl group optionally contains 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^5$ groups are optionally fused to a $C_6$–$C_{10}$ aryl group, a $C_5$–$C_8$ saturated cyclic group, or a 4–10 membered heterocyclic group; and said alkyl, cycloalkyl, aryl and heterocyclic $R^5$ groups are optionally substituted by 1 to 5 substituents independently selected from halo, cyano, nitro, difluoromethoxy, trifluoromethyl, trifluoromethoxy, azido, —NR$^7$SO$_2$R$^9$, —SO$_2$NR$^6$R$^7$, —C(O)R$^6$, —C(O)OR$^6$, —OC(O)R$^6$, —NR$^7$C(O)OR$^9$, —NR$^7$C(O)R$^6$, —C(O)NR$^6$R$^7$, —NR$^6$R$^7$, —OR$^6$, C$_1$–C$_{10}$ alkyl, —(CH$_2$)$_m$(C$_6$–C$_{10}$ aryl), and —(CH$_2$)$_m$ (4–10 membered heterocyclic), wherein m is an integer ranging from 0 to 4;

each R$^6$ is independently selected from H, C$_1$–C$_{10}$ alkyl, C$_3$–C$_{10}$ cycloalkyl, —(CH$_2$)$_m$(C$_6$–C$_{10}$ aryl), and —(CH$_2$)$_m$(4–10 membered heterocyclic), wherein m is an integer ranging from 0 to 4; said alkyl group optionally includes 1 or 2 hetero moieties selected from O, —S(O)$_j$— wherein j is an integer ranging from 0 to 2, and —N(R$^7$)— with the proviso that two O atoms, two S atoms, or an O and S atom are not attached directly to each other; said cycloalkyl, aryl and heterocyclic R$^6$ groups are optionally fused to a C$_6$–C$_{10}$ aryl group, a C$_5$–C$_8$ saturated cyclic group, or a 4–10 membered heterocyclic group; and the foregoing R$^6$ substituents, except H, are optionally substituted by 1 to 5 substituents independently selected from halo, cyano, nitro, difluoromethoxy, trifluoromethyl, trifluoromethoxy, azido, —C(O)R$^7$, —C(O)OR$^7$, —OC(O)R$^7$, —NR$^7$C(O)R$^8$, —C(O)NR$^7$R$^8$, —NR$^7$R$^8$, hydroxy, C$_1$–C$_6$ alkyl, and C$_1$–C$_6$ alkoxy;

each R$^7$ and R$^8$ is independently H or C$_1$–C$_6$ alkyl; and, R$^9$ is selected from the substituents provided in the definition of R$^6$ except H.

Preferred compounds of formula 1 include those wherein R$^1$ and R$^2$ are taken together to form =N—OR$^3$, and R$^3$ is C$_1$–C$_4$ alkyl, C$_2$–C$_4$ alkenyl, —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from nitro, halo, C$_1$–C$_3$ alkoxy, C$_1$–C$_4$ alkyl, trifluoromethyl, acetamido, tert-butoxycarbonylamino, tert-butoxycarbonylaminomethyl, tert-butoxycarbonyl, —NR$^6$R$^7$, phenyl, cyclohexyl, carboxy, aminomethyl, difluoromethoxy, trifluoromethoxy, cyano, piperidinyl, morpholino, phenoxy, and phenylthio.

Other preferred compounds of formula 1 include those wherein R$^1$ and R$^2$ are taken together to form =N—OR$^3$, and R$^3$ is —(CH$_2$)$_t$(C$_6$C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from nitro, halo, C$_1$–C$_3$ alkoxy, C$_1$–C$_4$ alkyl, difluoromethoxy, trifluoromethyl, acetamido, tert-butoxycarbonyl, tert-butoxycarbonylamino, —NR$^6$R$^7$, phenyl, cyclohexyl, carboxy, tert-butoxycarbonylaminomethyl, aminomethyl, trifluoromethoxy, cyano, piperidinyl, morpholino, phenoxy, and phenylthio.

Other preferred compounds of formula 1 include those wherein R$^1$ is H, R$^2$ is —NR$^3$R$^4$, R$^4$ is H or methyl, and R$^3$ is —(CH$_2$)$_t$(C$_6$–C$_{10}$ aryl) or —(CH$_2$)$_t$(4–10 membered heterocyclic), wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

Other preferred compounds of formula 1 include those wherein R$^1$ is H, R$^2$ is —NR$^4$C(O)R$^3$, R$^4$ is H, and R$^3$ is C$_3$–C$_6$ cycloalkyl, —(CH$_2$)$_t$(C$_6$ C$_{10}$ aryl) or —(CH$_2$)$_t$(4–10 membered heterocyclic), wherein t is an integer ranging from 0 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from halo, C$_1$–C$_3$ alkoxy, C$_1$–C$_4$ alkyl, and trifluoromethyl.

Other preferred compounds of formula 1 include those wherein R$^1$ and R$^2$ are taken together to form =CR$^4$C(O)OR$^3$ or =CR$^4$C(O)NR$^3$R$^4$, R$^4$ is H, and R$^3$ is H, C$_1$C$_6$ alkyl, C$_3$–C$_6$ cycloalkyl, —(CH$_2$)$_t$(4–10 membered heterocyclic), or —(CH$_2$)$_t$(C$_6$–C$_{10}$ aryl) wherein t is an integer ranging from 0 to 2, the aryl group is optionally fused to a 5 or 6 membered heterocyclic group, the heterocyclic group is optionally fused to a benzene ring, and the foregoing R$^3$ groups, except H but including said optionally fused moieties, are optionally substituted by 1 to 5 substituents independently selected from halo, C$_1$–C$_3$ alkoxy, C$_1$–C$_4$ alkyl, —NR$^6$R$^7$ and trifluoromethyl.

Other preferred compounds of formula 1 include those wherein R$^1$ is H, R$^2$ is —OR$^3$, and R$^3$ is C$_1$–C$_4$ alkyl, —(CH$_2$)$_t$(4–10 membered heterocyclic), or —(CH$_2$)$_t$ (C$_6$–C$_{10}$ aryl) wherein t is an integer ranging from 1 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from halo, C$_1$–C$_3$ alkoxy, C$_1$–C$_4$ alkyl, cyclohexyl, cyano, trifluoromethyl, benzyloxy and trifluoromethyl.

Other preferred compounds of formula 1 include those wherein R$^1$ is H, R$^2$ is —OC(O)NR$^3$R$^4$, R$^4$ is H, and R$^3$ is —(CH$_2$)$_t$(C$_5$–C$_{10}$ aryl) wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

Specific preferred compounds of formula 1 include those selected from the group consisting of 5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-2-yl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-phenylmethyloxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-phenylmethyloxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-

(E)-propenyl]amino]-1,2-O-methylene-D-neo-inositol, (E)-O-[(4-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-pyridinyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-(4-morpholinyl)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[cyclohexylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(furan-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[[(3-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-cyclohexylphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-aminophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[[(4-aminomethyl)phenyl]methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[3-(4-chlorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O[3-(4-chlorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-(trifluoromethoxy)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propeny(]amino]-1,2-O-methylene-D-neo-inositol, (E)-O-[(4-(1-piperidinyl)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-fluorophenyl)methyl]oxime;

5-Deoxy-5-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]1,2-O-methylene-D-neo-inositol, (E)-O-[2-(phenylthio)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-5-yl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-5-yl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-phenylpyrimidin-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluoro-4-methoxyphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dihydro-2H-1-benzopyran-4-yl)methyl]oxime;

5-Deoxy-5-[[3-[4-[(5,6-dideoxy-5-(methyl(phenymethyl)amino-a-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(5,6-dideoxy-5-phenylamino-a-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[3-[4-[(2,6-dideoxy-5-O-[(3,4-dichlorophenyl)methyl]-β-D-ribo-furanos-1-yl)oxy[-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-2-yl)methyl]oxime;

5-Deoxy-5-[[3-[4-[(5-methyl-β-D-erythro-hept-5-(E)-enofuranuron-1-ylic acid)oxy]-3-hydroxyphenyl]-2-methyl-1oxo-2-(E)-propenyl]amino]-1,2-O-methylene-D-neo-inositol, ethyl ester;

5-Deoxy-5-[[3-[4-[[N-(furan-2-yl)methyl]-(5-methyl-β-D-erythro-hept-5-(E)-enofuranuron-1-yl-amide)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(phenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(2-propen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(2-propen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methytene-D-neo-inositol, (E)-O-[(4-methylphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methoxyphenyl)methyl]oxime;

5-Deoxy-5-[[3-[4-[(2,6-dideoxy-β-D-erythro-hexfuranos-5-ulos-1-yl)oxy]-3-hydroxyphenyl]-2-methyl-1-oxo-2-(E)-propenyl]amino]-1,2-O-methylene-D-neo-inositol, (E)-O-[(3-(trifluoromethyl)phenyl)methyl]oxime;

5-Deoxy-5-[[3-[4-[(2,6-dideoxy-5-O-[(4-chlorophenyl)methyl]-β-D-ribo-furanos-1-yl)oxy[-3-hydroxyphenyl]-2-methyl-1-oxo-2-(E)-propenyl]amino]-1,2-O-methylene-D-neo-inosotol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[diphenylmethyl]oxime;

5-Deoxy-5-[[3-[4-[(2,6-dideoxy-5-phenylcarbamate-β-D-ribo-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-5-[(3,4-dichlorophenyl)methyl]carbamate-β-D-ribo-furanos-1-yl)oxyl-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-5-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-[(4-chloro-3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino-]1,2-O-methylene-D-neo-inositol, (Z)-O-[(4-chloro-1,3-benzodioxol-5-yl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-6-yl )methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-chloro-1,2,3,4-tetrahydronaphthalen-1-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-chloro-1,2,3,4-tetrahydronaphthalen-1-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-fluoro-1,2,3,4-tetrahydronaphthalen-1-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-fluoro-1,2,3,4-tetrahydronaphthalen-1-yl) oxime;

5-Deoxy-5-[[3-[4-[(2,6-dideoxy--D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-chloro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-chloro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-chloro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-chloro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-fluoro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-fluoro-3,4-dihydro-2H-1-benzopyran-4-yl) oxime;

5-Deoxy-5-[[3-(4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-fluoro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-fluoro-3,4-dihydro-2H-1-benzopyran-4-yl) oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-2-yl)methyl]oxime;

5-Deoxy-5-[[3-[4-((2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenylmethyl)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenylmethyl)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenoxy)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenoxy)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-Phenylthiaz-2-yl) methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-Phenylthiaz-2-yl) methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(2,4-difluorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(2,4-difluorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3,4-difluorophenyl)ethyl]oxime;

5-Deoxy-5-[[3-[4-[(2,6-dideoxy-β-D-erythro-hexofuranos-5-ulos-1-yl)oxy]-3hydroxyphenyl]-2-methyl-1-oxo-2-(E)-propenyl]amino]-1,2-O-methylene-D-nea-inositol, (Z)-O-[1-(2,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl]-1-oxo-2-(E)-propenyl]amino]-1,2-O-methylene-D-neo-inositol, (E)-O-[1-(2,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3,5-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3,5-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3-chloro-2,6-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3-chloro-2,6-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2,6-difluorophenyl)methyl]oxime;

5-Deoxy-5-[[3-[4-[((2,6-dideoxy -β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2,6-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlororophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluororophenyl)]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(phenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(phenyl)oxime;

5-Deoxy-5[4-[(2,6-dideoxy-β-D-erythro-hexofuranos-5-ulos 1-yl)oxy]-3-hydroxypenyl]-2-methyl-1-oxo-2-(E)-propenyl]amino]-1,2-O-methylene-D-neo-inositol, (Z)-O-(3-chloro-4-fluorophenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5(4-(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,1,3-benzoxadiazol-5-yl)methyl]oxime;

5-Deoxy-5(4-[(2,6-dideoxy-β-D-erythro-hexofuranos-5-ulos-1-yl)oxy]-3-hydroxyphenyl]-2-methyl-1-oxo-2-(E)-propenyl]amino)-1,2-O-methylene-D-neo-inositol, (E)-O-[(2,1,3-benzoxadiazol-5-yl)methyl]oxime;

5-Deoxy-5[4-[(2,6-dideoxy-β-D-erythro-hexofuranos-5-ulos-1-yl)oxy]-3-hydroxyphenyl]-2-methyl-1oxo-2-(E)-propenyl]amino]-1,2-O-methylene-D-neo-inositol, (E)-O-[(2,3,5,6-tetrafluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5[4-(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-3-yl)methyl]oxime;

5-Deoxy-5[4-(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-3-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluoro-6-methoxyphenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluoro-6-methoxyphenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-thiophen-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-thiophen-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-thiophen-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-[(5-chloro-thiophen-2-yl)methyl]oxime;
and the pharmaceutically acceptable salts, prodrugs and solvates of said compounds.

In a more specific embodiment, the present invention includes the following compounds:

5-Deoxy-5[4-[(2,6-dideoxy-β-D-erythro-hexofuranos-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5[4-[(2,6-dideoxy-β-D-eythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5(4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5(4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5(4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methy]oxime;

5-Deoxy-5[4-[(2,6-dideoxy-β-D-erythro-hexofuranos--ulos-1-y)oxy]-3-hydroxypenyl]-2-methyl-1-oxo-2-(E)-propenyl]amino]-1,2-O-methylene-D-neo-inositol, (E)-O-[(4-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-O-neo-inositol, (E)-O-[(3,4-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,²-O-methylene-D-neo-inositol, (E)-O-[(2,3-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

5-Deoxy-5-[[3-[4-[((2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2,6-difluorophenyl)methyl]oxime;

5-Deoxy-5-[[3-[4-[((2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2,6-difluorophenyl)methyl]oxime;

5-Deoxy-5-[[3-(4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

and the pharmaceutically acceptable salts, prodrugs and solvates of said compounds.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, or a pharmaceutically acceptable salt thereof, and a pharmaceutically acceptable carrier.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1 or a pharmaceutically acceptable salt thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or Peptostreptococcus spp.; pharyngitis, rheumatic fever, and glomerulonephritis related to infection by *Streptococcus pyogenes*, Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae;* blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative staphylococci (i.e., *S. epidermidis, S. hemolyticus,* etc.), *Streptococcus pyogenes , Streptococcus agalactiae,* Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus aureus,* coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and toxic shock syndrome), or Groups A, B, and C streptococci; ulcers related to infection by *Helicobacter pylon;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* infections caused by *Mycobacterium tuberculosis, M. leprae, M. paratuberculosis, M. kansasii,* or *M. chelonei;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis or cardiovascular disease related to infection by *Helicobacter pylori* or *Chlamydia pneumoniae.* Bacterial infections and protozoal infections, and disorders related to such infections, which may be treated or prevented in animals include the following: bovine respiratory disease related to infection by *P. haemolytica, P. multocida, Mycoplasma bovis,* or Bordetella spp.; cow enteric disease related to infection by protozoa (i.e., coccioia, cryptosporidia, etc.); dairy cow mastitis related to infection by *S. aureus, Strep. uberis, Streptococcus agalactiae. Streptococcus dysgalactiae,* Corynebacternum, or Enterococcus spp.; swine respiratory disease related to infection by *A. pleuro.. P. multocida,* or Mycoplasma spp.; swine enteric disease related to infection by, *Lawsonia intracellularis,* Salmonella, or *Serpulina hyodysinteriae;* cow footrot related to infection by Fusobacterium spp.; cow hairy warts related to infection by *Fusobacterium necrophorum* or *Bacteroides nodosus;* cow pink-eye related to infection by *Moraxella bovis;* cow premature abortion related to infection by protozoa (i.e. neosporium); skin and soft tissue infections in dogs and cats related to infection by *S. epidermidis, S. intermedius,* coagulase neg. Staphylococcus or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Said alkyl group may include one or two double or triple bonds. It is understood that for said alkyl group to include a carbon-carbon double or triple bond at least two carbon atoms are required in said alkyl group.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3 -dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyt, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations of the —$OR^3$ group connected to the nitrogen where $R^1$ and $R^2$ are taken together as an oxime moiety of the formula =N—$OR^3$. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^4C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19. 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Selective introduction of prodrug side chains can be carried out on the hydroxy groups of the hygromycin A core molecule. For instance, exhaustive silylation of the six hydroxy groups of hygromycin A can be carried out, for instance with tert-butyl dimethylsilyl chloride. Subjection of the hexasilyl derivative to the action of potassium carbonate in methanol at room temperature selectively removes the phenolic silyl group, allowing further selective modification at that position.

DETAILED DESCRIPTION OF THE INVENTION

The preparation of the compounds of the present invention is illustrated in the following Schemes.

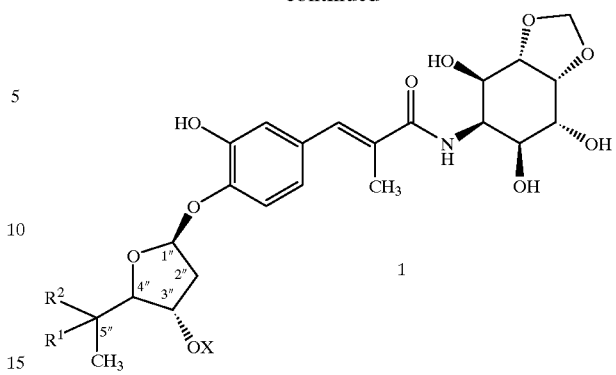

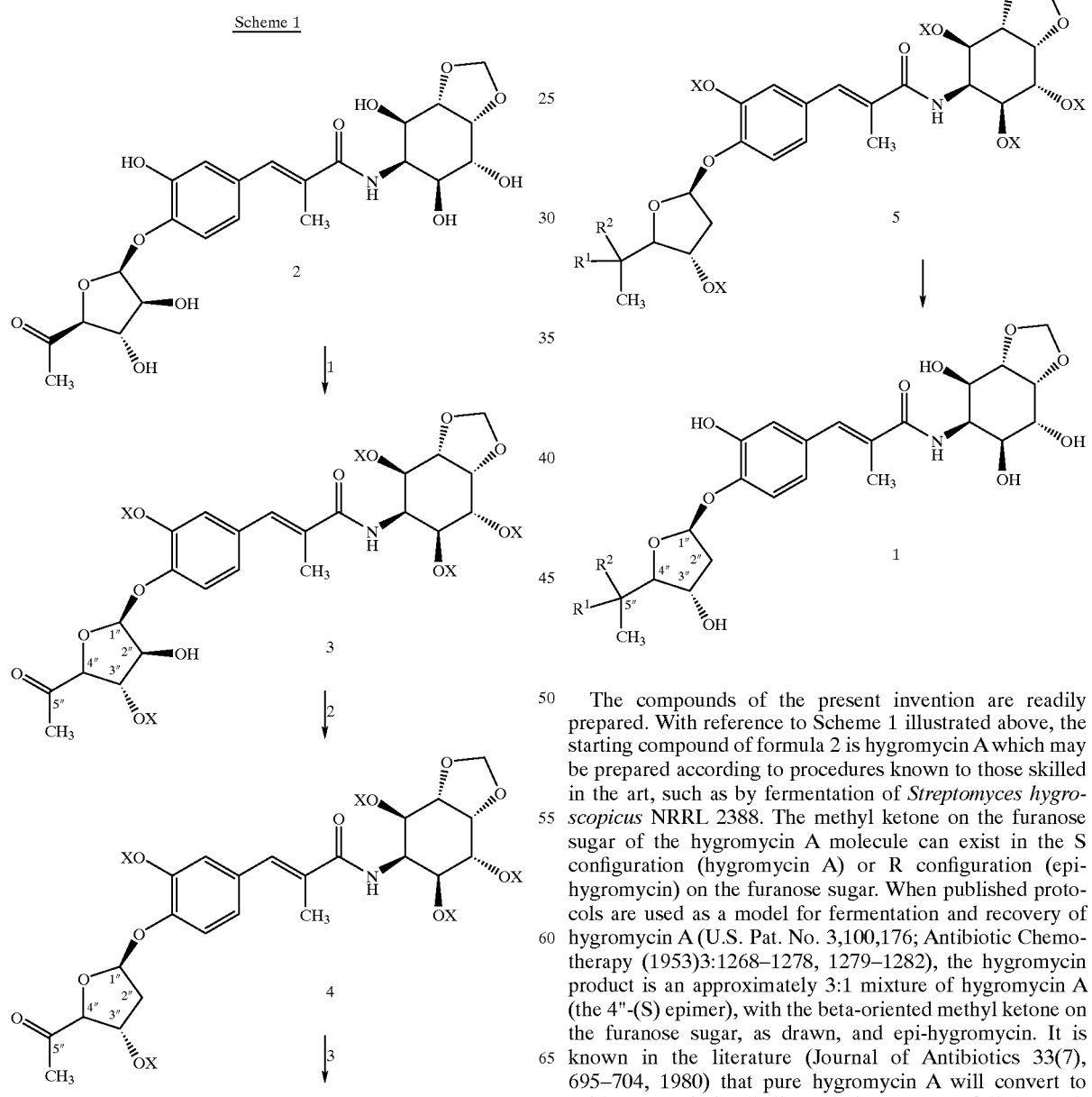

The compounds of the present invention are readily prepared. With reference to Scheme 1 illustrated above, the starting compound of formula 2 is hygromycin A which may be prepared according to procedures known to those skilled in the art, such as by fermentation of *Streptomyces hygroscopicus* NRRL 2388. The methyl ketone on the furanose sugar of the hygromycin A molecule can exist in the S configuration (hygromycin A) or R configuration (epi-hygromycin) on the furanose sugar. When published protocols are used as a model for fermentation and recovery of hygromycin A (U.S. Pat. No. 3,100,176; Antibiotic Chemotherapy (1953)3:1268–1278, 1279–1282), the hygromycin product is an approximately 3:1 mixture of hygromycin A (the 4"-(S) epimer), with the beta-oriented methyl ketone on the furanose sugar, as drawn, and epi-hygromycin. It is known in the literature (Journal of Antibiotics 33(7), 695–704, 1980) that pure hygromycin A will convert to epi-hygromycin in alkaline solutions. By carefully controlling the pH below 6.9 during the fermentation, and the pH, temperature and solvent exposure during the purification process, the final recovered product may be improved to a 14.1 ratio of hygromycin A:epi-hygromycin. Using this material, substantially single isomers derived from the 4"-(S) hygromycin may be prepared for use as templates for further synthetic modification.

Hygromycin A enriched for the 4"-(S) epimer is produced by fermentation of Streptomyces hygroscopicus NRRL2388, or mutants thereof, in media with pH controlled at less than 6.9, preferably 6.2 to 6.7, throughout the process. The medium contains assimilable sources of carbon, nitrogen and trace elements, as known to those skilled in the art. The fermentation is run at a temperature of about 25–35° C. preferably about 29° C. The fermentation is monitored by chromatography, for example high pressure liquid chromatography. Incubation is continued until the yield of the compound reaches a maximum, generally for a period of about 3 to 10 days, preferably about 4 to 6 days.

The formation of epi-hygromycin is minimized during the purification process by using an aqueous buffer (rather than unbuffered water) and controlling the pH of the active streams to near 6.0. Epi-hygromycin formation is also minimized by minimizing the time the recovered material is subject to higher temperatures. Thus, where it is necessary to reduce solvent concentrations, it is preferred to dilute active streams with the aqueous buffer and avoid use of rotary evaporation at elevated temperatures. Also, as means of avoiding higher temperatures, a resin column may be used to concentrate the active solution prior to the final purification step in order to reduce the volume of solution that requires boiling. The final purification step in the process is the concentration of the active cuts to solids using vacuum and a bath temperature of about 35–50° C. The period in which the solution is subject to elevated temperatures may be minimized by boiling in stages.

The compounds of formula 1 can be prepared from the compound of formula 4. In this process, the compound of formula 3 (wherein X is a protecting group as described below), is prepared by protection of all of the hydroxy groups of hygromycin A, with the exception of the hydroxy at the 2" carbon (C-2"), as their silyl ethers using an appropriate reagent such as triethylsilyl chloride (TESCI), trimethylsilyl chloride (TMSCI) or tert-butyldimethysilyl chloride (TBDMSCI). The preferred method is 10 eq of TBDMSCI and imidazole in N,N-dimethylformamide (DMF) at a temperature of 25–40° C. for 12–36 hours. The compound of formula 4 is then prepared by removal of the hydroxy group using the method of Barton et al., *J. Chem Soc., Perkin Trans.*/1975, 1574. The preferred method in this case is the method of Génu-Oellac et al., *Carbohydrate Res.* 1991, 216, 249.

The compounds of formula 1 wherein $R^1$ and $R^2$ are taken together to form an oxime of the formula $=NOR^3$, wherein $R^3$ is as defined above, may be prepared by treating the compound of formula 4 with a hydroxylamine of the formula $R^3ONH_2$, using the free base or salt of the hydroxylamine. preferably the free base of the hydroxylamine. The reaction is carried out in an inert solvent, such as methanol, with addition of base, such as $K_2CO_3$, if the salt, for instance the HCl salt, of the hydroxylamine is used, at a temperature ranging from about 0° C. to 65° C., preferably from 0° C. to 25° C. The protecting groups are then removed with acid, such as acetic acid, hydrogen fluoride, hydrogen fluoride-pyridine complex, or a fluoride source, such as tetrabutylammonium fluoride (TBAF). The hydroxylamine of formula $R^3ONH_2$ may be prepared using one or more procedures disclosed in Bioconjugate Chemistry (1990), 2, 96; Journal of Pharmaceutical Science (1969) 58, 138; and Chem. Pharm. Bull (1967) 15, 345.

The compounds of formula 1 wherein $R^1$ and $R^2$ are taken together to form ketone of the formula $=O$, may be prepared by treating the compound of formula 4 with acid, such as acetic acid, hydrogen fluoride, hydrogen fluoride-pyridine complex, or a fluoride source, such as tetrabutylammonium fluoride (TBAF) preferably hydrogen fluoride-pryidine complex.

The compounds of formula 1 wherein $R^1$ is H and $R^2$ is —$NR^3R^4$, wherein $R^3$ and $R^4$ are as defined above, can be synthesized by reductive amination at the C-5" ketone site of the compound of formula 4. Combination of $R^4NH_2$ and the compound of formula 4 in an inert solvent and treatment with a reducing agent such as $NaBH_4$, $NaBH(OAc)_3$ (Ac is acetyl), or $NaCNBH_3$ provides the product with $R^3$=H. To convert $R^3$ to a group other than H, a second reductive amination can be carried out with an appropriate aldehyde (or ketone) of the formula $R^3C(O)H$. An Eschweiler-Clark reaction may be followed to introduce a methyl group as the $R^3$ substituent. To provide an amide group such as where $R^1$ is H and $R^2$ is —$NR^4C(O)R^3$, an amine of the formula —$NHR^4$ may be introduced as described above and then an acyl moiety of the formula —$C(O)R^3$ may be introduced by treating the intermediate with an activated form of the carboxylic acid, such as $R^3COCl$ or $R^3C(O)OC(O)R^3$, or by using an amide coupling agent such as 2-ethoxy-1-ethoxycarbonyl-1,2-dihydroquinoline (EEDQ), 1,1'-carbonyl-diimidazole (CDI), or a carbodiimide such as 1,3-dicyclohexylcarbodiimide (DCC). For all of the above processes the protecting groups are removed with acid. such as acetic acid, hydrogen fluoride, hydrogen fluoride-pyridine complex, or a fluoride source, such as TBAF as the final step.

Compounds of formula 1 where $R^1$ is H and $R^2$ is —$NR^4C(O)R^3$, wherein $R^4$ is H and $R^3$ is as defined above, may be prepared through use of the primary amine derived from reductive amination of the compound of formula 4 with an ammonia equivalent, for instance through the use of ammonium acetate and sodium cyanoborohydride or sodium triacetoxyborohydride. Alternatively, this primary amine can be prepared via the corresponding azide: (1) the C-5" ketone of the compound of formula 4 is reduced, for instance with sodium borohydride; 2) the resulting alcohol is transformed into the mesylate, for instance through the action of methanesulfonyl chloride and triethylamine; 3) the mesylate is displaced by azide, for example using sodium azide in DMF; and 4) the azide is reduced to the primary amine using for instance triphenylphosphine followed by aqueous hydrolysis.

Reaction of the primary amine with an activated form of $R^3C(O)OH$, for instance $R^3C(O)Cl$ or $R^3C(O)OC(O)R^3$, provides the corresponding amide. Alternatively, amide coupling reagents can be used with $R^3C(O)OH$, such as 1-(3-dimethylaminopropyl)-3-ethyl-carbodiimide (EDC), diethyl phosphoryl cyanide (DEPC), DCC, CDI or EEDQ. Finally, any protecting groups are removed using an acid, such as acetic acid, hydrogen fluoride, hydrogen fluoride-pyridine complex, or fluoride ion, such as TBAF.

To incorporate an $R^4$ group other than H, the amide referred to above may be alkylated after protecting any free hydroxyl groups, for instance as silyl ethers. The alkylation may be carried out with a base and an alkylating agent, such as sodium hydride and an appropriate bromide of the formula $R^4$—Br. Deprotection of the hydroxyl groups is then carried out with an acid, such as acetic acid, hydrogen fluoride, hydrogen fluoride-pyridine complex, or fluoride ion, such as TBAF.

Alternatively, a reductive amination can be carried out on the compound of formula 4 with $R^4NH_2$, mediated by sodium triacetoxyborohydride or sodium cyanoborohydride. The resulting secondary amine can be acylated as described above, with an activated form of $R^3C(O)OH$, or reacted with $R^3C(O)OH$ using an amide coupling reagent. Deprotection of the hydroxyl groups is then effected as described above.

With reference to Scheme 2, compounds of formula 1 where $R^1$ is H and $R^2$ is —$OR^3$, wherein $R^3$ is an alkyl group or a substituted alkyl group, may be prepared by alkylation of the corresponding alcohol of the compound of formula 5 (wherein X is a protecting group as described above) wherein $R^1$ is hydroxyl and $R^2$ is hydrogen. In this process the C-5" ketone moiety of compound of formula 4 is reduced using an appropriate reducing agent such as sodium borohydride. The resulting C-5" alcohol can then be alkylated with $R^3$—Z, wherein Z is a leaving group such as Cl, Br, I or methanesulfonate, in the presence of a base, such as sodium hydride or potassium ted-butoxide. The protecting groups are then removed with acid, such as acetic acid, hydrogen fluoride, hydrogen fluoride-pyridine complex, or a fluoride source, such as TBAF.

Compounds of formula 1 where $R^1$ is H and $R^2$ is —$OR^3$, wherein $R^3$ is an aromatic or heterocyclic moiety, may be prepared via a Mitsunobu reaction. The C-5" alcohol, prepared as described above, is subjected to a Mitsunobu reaction with $R^3OH$, mediated by triphenylphosphine and diethyl azodicarboxylate. The resulting ether is then deprotected as described above.

Alternatively, when $R^1$ is H and $R^2$ is —$OR^3$, wherein $R^3$ is an aromatic or heterocyclic moiety, the C-5" alcohol derived from the compound of formula can be transformed into a leaving group, for instance the bromide or mesylate derivative. The leaving group can then be displaced by $R^3OH$ using a base such as sodium hydride, potassium tert-butoxide or potassium carbonate.

Compounds of formula 1 where $R^1$ is H and $R^2$ is —$OC(O)NR^3R^4$ may be prepared by reaction of the C-5" alcohol derived from the compound of formula 5 as described above with isocyanate $R^3NCO$ in toluene at temperatures from 40° C. to 110° C., preferably 50–80° C. Addition of dimethylaminopyridine and triethylamine to the reaction may be advantageous. The product of this reaction, which has $R^4$ equal to H, may be alkylated to give $R^4$ equal to $C_1$–$C_{10}$ alkyl through use of a base such as sodium hydride and an alkylating agent such as a bromide of the formula $R^4$—Br. Deprotection of the hydroxyl groups can then be carried out by use of fluoride ion, such as TBAF.

Compounds of formula 1 wherein $R^1$ and $R^2$ are taken together to form =$CR^4C(O)R^3$, =$CR^4C(O)OR^3$, or =$CR^4C(O)NR^3R^4$, wherein $R^3$ and $R^4$ are as defined above, may be prepared through the corresponding α,β-unsaturated ester intermediates derived from Wittig or Horner-Emmons Wittig olefination of the C-5" ketone of the compound of formula 4. For instance, (carbethoxymethylene) triphenylphosphorane or (carbethoxyethylidene) triphenylphosphorane can be reacted with the compound of formula 4 to provide the unsaturated ethyl ester. Hydrolysis of this ester, for instance with sodium hydroxide, provides the corresponding carboxylic acid (compound of formula 5 wherein $R^1$ and $R^2$ are taken together to form =CHC(O)OH). At this point, the hydroxy groups which have been liberated in the previous step can be protected, for instance as their TES or TBDMS ethers. To prepare the esters described above, this carboxylic acid can be esterified with $R^3OH$, for instance through the action of DCC and 4-dimethylaminopyridine (DMAP), or CDI and a catalytic base such as sodium ethoxide. Deprotection of the hydroxyl groups is then carried out with an acid, such as acetic acid, hydrogen fluoride, hydrogen fluoride-pyridine complex, or fluoride ion, such as TBAF.

Compounds of formula 1 wherein $R^1$ and $R^2$ are taken together to form =$CR^4C(O)NR^3R^4$ may be formed by treating the above carboxylic acid intermediate (compound of formula 5 wherein $R^1$ and $R^2$ are taken together to form =CHC(O)OH) with an amine of the formula $R^3NH_2$ with the use of an amide coupling agent such as DCC, CDI, EEDQ, DEPC, or EDC. On the protected derivative, $R^4$ can be introduced via alkylation, for instance with a base such as sodium hydride or potassium tert-butoxide and an alkylating agent such as $R^4$—X where is X is Br, Cl or methanesulfonate. Deprotection of the hydroxyl groups is then as described above.

The ketone of formula 1 ($R^1$ and $R^2$ are taken together to form =$CR^4C(O)R^3$) can be prepared either by direct Wittig or Horner-Emmons reaction of the compound of formula 4 with for example the corresponding $R^3C(O)CHR^4$—$PPh_3$ (Ph is phenyl) or $R^3C(O)CHR^4$—$P=O(OEt)_2$ (Et is ethyl) reagent. Alternatively, the compound of formula 5 wherein $R^1$ and $R^2$ are taken together to form =CHC(O)OH can be transformed into the Weinreb amide, for instance through treatment with CDI and N,O-dimethylhydroxylamine. This amide can then be reacted with $R^3$—M, where M is a metal ion such as Li or MgBr, to generate the ketone. The aldehyde (ketone structure where $R^3$ is H) can be prepared by reaction of the Weinreb amide with a hydride source, such as diisobutylaluminum hydride (DIBAL) or $LiAlH_4$.

Compounds of formula 1 wherein $R^1$ and $R^2$ are taken together to form =$CR^4R^3$, wherein $R^3$ and $R^4$ are as defined above, may be prepared by a Wittig or Hormer-Emmons reaction of the yield of $R^4$—$CH(PPh_3)$—$R^3$ or $R^4$—CH ($P=O(OEt)_2$)—$R^3$ with the compound of formula 4. The protecting groups can then be removed as described above.

Alternatively, either the ketone or aldehyde of formula 5, wherein $R^1$ and $R^2$ are taken together to form =$CR^4C(O)R^3$ and =$CR^4C(O)H$ respectively, can be utilized as an intermediate. These compounds can be accessed via Wittig or Horner-Emmons reaction with an oxygenated triphenylphosphonium salt or phosphorane such as $Ph_3P$—$C(R^3)$ OMe (Me is methyl). The resulting enol ether can be hydrolyzed with mild acid, such as acetic acid or dilute HCl, to provide the aldehyde or ketone. The aldehyde or ketone can then be reacted with an organometallic derivative $R^4$—M, where M is, for example, Li or MgBr, to provide the corresponding alcohol, which can be dehydrated under the action of methanesulfonyl chloride to provide the corresponding olefin. Deprotection as described above then provides the compound of formula 1 wherein $R^1$ and $R^2$ are taken together to form =$CR^4R^3$.

The compound of formula 1 wherein $R^1$ and $R^2$ are taken together to form =$CR^4R^3$ and $R^4$ is aryl or heteroaryl and $R^3$ does not equal hydrogen, may be prepared using a palladium-catalyzed process. Conversion of compound of formula 5 wherein $R^3$ is —$CH(COR^3)$ to an activated enol ether, for example the enol triflate, provides an intermediate which can be coupled in a Suzuki or Stille-type palladium-catalyzed process with aryl or heteroaryl boronic acids $R^4B(OH)_2$ or aryl tin species, for example $R^4SnMe_3$ or $R^4SnBu_3$ (Bu is butyl) to provide the unsaturated aryl derivatives. Deprotection as described above then provides the final compound.

The compounds of the present invention have asymmetric carbon atoms. Such diastereomeric mixtures can be separated into their individual diastereomers on the basis of their physical chemical differences by methods known to those skilled in the art. for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case. stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

ASSAY

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents.

According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1–2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances. dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn. potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as P-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below. In the preparations and examples. "rt" means room or ambient temperature which is a temperature within the range of about 20–25° C.

PREPARATION 1

Five (5) mL of a frozen lot (stored at −80° C. in 20% glycerol/80% inoculum medium) of the culture Streptomyces hygroscopicus NRRL 2388 was used to inoculate 1 L of hygromycin inoculum medium (Corn Products Corp. cerelose 13 g/L, Hubinger starch 7 g/L, Roquette corn steep solids 3 g/L, Sheffield Brand Products NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 3 days at 29° C. with 200 rpm agitation on a 2-inch-throw shaker. This grown culture was used to inoculate 8 L of sterile hygromycin fermentation medium (Albaglos calcium carbonate 1 g/L, Sheffield Brand Products NZ Amine YTT 5 g/L, Hubinger's starch 20 g/L, Archer Daniels Midland Nutrisoy flour 10 g/L, Dow Chemical P2000 defoamer 1 ml/L, Baker $CoCl_2.6H_2O$ 0.002 g/L, Colfax soybean oil 2 ml/L, cerelose 10 g/L, NaCl 5 g/L, pH to 7.0 before autoclave) in a 14 liter fermentor jar (New Brunswick Microferm, New Brunswick, N.J.) equipped with two 4.75-inch Rushton impellers, spaced 3.75 inches from each other. The broth was incubated at 29° C. with an aeration rate of 8 L/minute, and with stirring at 800 rpm. To minimize formation of epi-hygromycin, the pH was maintained between 6.5 and 6.9 for 126 hours, then to 6.2 to 6.6 with $H_2SO_4$ (15%) for the rest of the run. The fermentation was harvested after 143 hours total incubation. At this time, the ratio was 31:1 hygromycin A to epi-hygromycin.

Six liters of broth from the above fermentation was centrifuged at 8000 rpm for approximately 15 minutes. After centrifugation, the pellet was discarded and the supernatant (at pH 6.4, assayed by HPLC to contain approximately 4.12 gms of hygromycin A activity) was loaded on a column packed with 500 gms of an XAD-16 resin (Rohm and Haas (Philadelphia, Pa.). The resin had previously been equilibrated with two bed volumes of 25 mM disodium phosphate, pH 6.0 ("buffer"). After loading, the column was washed with 2 bed volumes of buffer and 2 bed volumes of 80/20 buffer/methanol and the activity eluted with 5 bed volumes of 50/50 buffer/methanol. The cuts were assayed by HPLC and the cuts containing the bulk of the activity (2.730 gms of hygromycin A) were combined.

A part of this XAD-16 eluate (approximately 800 mg of hygromycin A) was diluted to 10% methanol by the addition of 1.8 liters of buffer and loaded on a 100 ml CG-161 column (TosoHaas (Montgomeryville, Pa.)) which had been equilibrated with 4 bed volumes of 90/10 buffer/methanol. The product was eluted with 6 bed volumes of 50/50 buffer/methanol. The cuts were assayed by HPLC and the active cuts were combined. The combined cut was evaporated to dryness and the solids assayed to be approximately 65% pure by weight. A small part of these solids were transferred for assay.

About 500 mg of the solids were mixed with 500 ml of water and 500 ml of ethyl acetate and stirred for 20 minutes. The two layers were separated and part of the aqueous layer was dried to obtain solids which were assayed to be approximately 52% purity by weight. Both these solids (#34945-280-1 and 281-1) were assayed by NMR and TLC and found to contain hygromycin A activity. In addition, the NMR showed a hygromycin A/epi-hygromycin ratio of approximately 15:1.

PREPARATION 2

Five (5) mL of a frozen lot (stored at −80° C. in 20% glycerol/80% inoculum medium) of the culture Streptomyces hygroscopicus NRRL 2388 was used to inoculate 1 L of Hygromycin inoculum medium (CPC International Inc. cerelose 13 g/L, Hubinger's starch 7 g/L, Roquette corn steep solids 3 g/L, NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 2 to 3 days at 290° C. with 200 rpm agitation on a 2-inch-throw shaker. Two five-hundred gallon, stainless steel fermentors were loaded with 380–400 gallons of the hygromycin fermentation medium (Mineral Technologies Calcium Carbonate 1 g/L, Sheffield Brand Products NZ Amine YTT 5 g/L, Hubinger's starch 20 g/L, Archer Daniels Midland Co., Soyflour 10 g/L, Dow Chemical P2000 defoamer 1 ml/L, Baker $CoCl_2.6H_2O$ 0.002 g/L, Colfax, Inc. soybean oil 2 gm/L, CPC International Inc. Cerelose 10 g/L, Cargill Inc. NaCl 5 g/L,). The medium was sterilized with 20 psig of steam for 60 minutes in the fermentors. After the medium was cooled using cooling coils in the fermentors, the pH was adjusted to 6.5–6.7. The fermentor conditions were set so that the airflow rate was 20 standard cubic feet per minute, the temperature was 28° C., the vent pressure was 5 psig, and the pH was maintained between 6.5–6.7 with 25% sodium hydroxide and 98% sulfuric acid. The agitation rates in the two fermentors were varied so as to maintain a dissolved oxygen level of greater than 20% of saturation level as measured in the broth immediately prior to inoculation. Upon setting the fermentor control conditions, five Fernbach inoculum flasks were combined in a sterile manner, into an 8 L aspirator bottle. This inoculum was then used for inoculation of a single, nominal, five-hundred gallon fermentor as described above. This procedure was repeated using 4 liters of inoculum so that one fermentor received four liters of inoculum and one fermenter received five liters of inoculum. Each fermentor ran for approximately 114 hours, at which time the fermentations were stopped. The broth pH was adjusted to 6.3 using 98% sulfuric acid and transferred from the fermentors for recovery.

The two fermentors referred to above (pH=6.3, having a ratio of hygromycin A to epi-hygromycin of approximately 51:1) were filtered on a ceramic filtration system. The filtrate (1450 gmsA, 506 gal) was loaded on a 70-gallon XAD-16 resin column. This column had been equilibrated previously with 4 bed volumes of a solution of trisodium phosphate buffer at pH 6.0 ("buffer"). After loading, the column was washed with 2 bed volumes of buffer and 2 bed volumes of 80/20 buffer/methanol. The activity was subsequently eluted from the column with 10 cuts (approximately 50 gallons each) of a solution of 50/50 buffer/methanol. The active cuts (approximately 1240 gmsA) were combined and diluted to a final concentration of 10% methanol by the addition of 1200 gallons of buffer. The use of dilution (rather than rotary evaporation) to reduce methanol concentration allowed the use of lower temperatures so as to minimize epi-hygromycin amounts, which tend to increase at higher temperatures. Half of this solution was loaded on a 40 liter CG-161 column (previously equilibrated with 4 bed volumes of a solution of 90/10 buffer/methanol). After loading, the column was washed with 4 bed volumes of 80/20 buffer/methanol and eluted with 5.5 bed volumes of 50/50 buffer/methanol. After regeneration and re-equilibration of the column, the second half of the activity was loaded on the column and eluted as described above. The combined cuts from both the runs (120 liters, approximately 1051 gmsA) were diluted to 10% methanol by the addition of buffer. This was re-loaded on the regenerated and re-equilibrated CG-161 resin column. Once the activity was adsorbed on the column, it was eluted with 4 bed volumes of methanol. This step served to both reduce the salts as well as increase the concentration of the sample prior to the final evaporation. The combined cuts from the final CG-161 column were evaporated to dryness to obtain a total of approximately 1 kgA of hygromycin A activity. The ratio of hygromycin A to epi-hygromycin in the final solids was about 14.5:1.

Experimental Procedures For Examples

Preparation of Compound of Formula 3

A solution of hygromycin A (1 eq.) in dimethylformamide (DMF, 0.1 M) was treated with imidazole (10 eq) and tert-butyldimethylsilyl chloride (10 eq) at 35° C. for 14–16 hours. The reaction was poured into water and extracted with ethyl acetate (EtOAc). The combined extracts were dried over MgSO4 and concentrated. The product was obtained after chromatography (5–15% EtOAc/hexanes).

Preparation of Compound of Formula 5

A solution of the compound of the formula 3 (1 eq.) in dichloroethane was treated with phenylthionochloroformate (3 eq.), pyridine (5 eq) and dimethylaminopyridine (0.05 eq.) at room temperature for 2–3 days. At the end of this time the reaction was diluted with methylene chloride, washed with 0.5 N HCl, saturated sodium bicarbonate and then brine. The organics were dried over MgSO, and concentrated. The desired 2"-thionocarbonate was obtained after chromatography (5–10% EtOAc/hexanes).

A solution of the above 2"-thionocarbonate (1 eq.) in toluene (0.1 M) was treated with α,α'-azobis(isobutyronitrile)(1 eq.) and tri-n-butyltinhydride (3 eq.) at 90° C. for 2 hours. The reaction was concentrated and chromatographed (5–10% EtOAc/hexanes) to provide the desired 2"-deoxy compound of formula 5.

Preparation of the Oxime Ethers, Examples 1–30

A solution of the compound of the formula 4 (1 eq.) in methanol (0.1 M) was treated with the appropriate hydroxylamine at 60° C. for 30 minutes to 1 hour. The reaction mixture was concentrated and the desired oximes were obtained after chromatography (generally 15% EtOAc/(toluene or hexanes)).

Removal of the silyl groups was accomplished by treatment of the above oxime with tetrabutuylamonium fluoride (10 eq.) in tetrahydrofuran at room temperature for 12–24 h. The concentrated reaction mixture was passed through a bed of ion exchange resin (Dowex 400 35 g resin per g starting material), and then the desired oxime was obtained as a mixture of E and Z isomers after chromatography (generally 5–15% methanol/chloroform).

Alternatively, removal of the silyl groups was accomplished by addition of a solution of tetrahydrofuran, pyridine, hydrogen fluoride-pyridine complex (65 ml, 16.5 ml, 8.25 ml; respectively) to a room temperature solution of the above oxime (6 mmole) in tetrahydrofuran (98 ml). The reaction was continued for 24–96 h and was quenched by the addition of solid sodium bicarbonate. The desired oxime was obtained as predominately the E isomer after chromatography (generally 5–15% methanol/chloroform).

In the case of example 10 compound of the formula 4 was deprotected by the above hydrogen fluoride-pyridine method.

Preparation of Hydroxylamine Reagents for Synthesis of Oxime Ethers, Examples 1–30

The majority of hydroxylamine reagents employed were either commercially available (generally as an acid salt), or prepared from the corresponding alcohol or halide via the methods outlined below:

1) Preparation of Phthalimide-protected Hydroxylamines

From the alcohol:

A Mitsunobu reaction with diethyl azodicarboxylate and triphenylphosphine was used to couple N-hydroxyphthalimide and the alcohol starting material, according to the procedure of E. Grochowski and J. Jurczak, *Synthesis* (1976) 682.

From the bromide or chloride:

Reaction of N-hydroxyphthalimide (1 equivalent) with the halide starting material (1.2–2 equivalents) was carried out in dimethyl sulfoxide (DMSO) solution, using potassium carbonate (0.6–2 equivalents) as base. The reactions were carried out at room temperature, generally by stirring overnight. Pouring the reaction mixture into cold water provided a precipitate, which was filtered to give the phthalimide-protected hydroxylamine. In many cases, this material was directly deprotected; silica gel chromatography can also be employed, using ethyl acetate-hexane mixtures, to purify the phthalimide-protected hydroxylamine.

2) Removal of the Phthalimide Protecting Group to Provide the Hydroxylamine

Deprotection of the phthalimide-protected hydroxylamine was effected by reaction with hydrazine hydrate (1–2 equivalents) in ethanol solution, at temperatures ranging from room temperature to reflux, for periods ranging from 30 minutes to overnight. The reaction mixture was filtered, and the filtrate concentrated. This crude product was either taken to the next step as is or further purified. Mixing the crude product with chloroform, removing solids by filtration and removal of solvent from the filtrate removes additional phthalhydrazide. Alternatively, the crude product was dissolved in 1 N hydrochloric acid, and washed with ether or ethyl acetate. The aqueous layer was basified with saturated potassium carbonate solution and extracted with ether or ethyl acetate. Drying of the final organic layers and removal of solvent provided the hydroxylamine product.

3) Preparation of 4-phenyl-chloromethylthiazole

4-Phenyl-thiazole-2-carbaldehyde was prepared by a method analogus to K. Inami and T. Shiba, Bull Chem Soc Jpn, 1985, 58, 352. The aldehyde was reduced to the corresponding alcohol using sodium borohydride in ethanol. The corresponding chloromethylthiazole was be prepared by treatment of the alcohol with thionyl chloride (4 equivalents) in methylene chloride at room temperature for 2–5 hours.

4) Preparation α-substituted Benzyl Alcohols 1-(3-Chloro-2,6-difluoro-phenyl)-ethanol and other phenylethanol derivatives (examples 11, 14, 15, 17, 18) were prepared by treatment of the corresponding phenyl-carboxaldehyde with methylmagnesiumbromide (1 equivalent) in THF at room temperature. These were then converted to the corresponding benzyl bromides by treatment with 48% HBr for 1–4 hours.

1-(3-Chloro-2,6-difluoro-phenyl)-carboxaldehyde was prepared from 3-Chloro-2,6-difluorobenzene with lithium diisopropylamide and N,N-dimethylformamide in a method similar to A. S. Cantrell, et al., J. Medicinal Chemistry 1996, 21,4261.

2,4-difluoroproiophenone (example 16) was reduced to the corresponding alcohol using sodium borohydride in ethanol.

5) Preparation of O-arylhydroxylamines

Substituted phenois were converted into the corresponding O-arylhydroxylamines through the use of mesitylenesulfonylhydroxylamine, as described by Y. Endo, K. Shudo and T. Okamoto, Synthesis 1980, 461.

Specific compounds prepared according to the above processes are illustrated in the table below. In the table, "Ex" means example, "Stereo" means oxime stereochemistry, "Mol Wt" means molecular weight, and "Mass Spec" means mass spectrometry.

TABLE

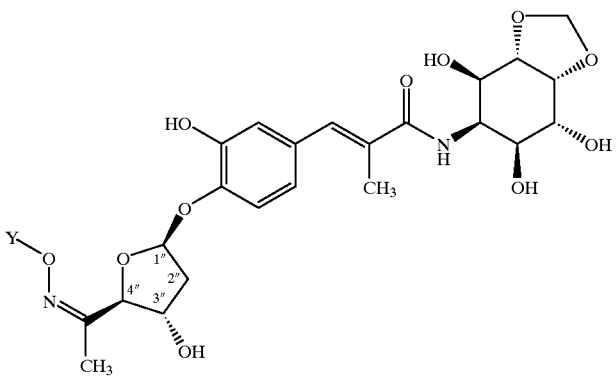

| Ex. | Y | Stereo | Mol Wt | Mass spec | 1H NMR peaks (CD$_3$OD) |
|---|---|---|---|---|---|
| 1 | 4-(chlorophenyl)methyl | E | 635 | 635.1 | δ=7.34–7.24(m, 5H), 7.00(d, J=8.3Hz, 1H), 6.91(s, 1H), 6.83(d, J =8.2Hz, 1H), 5.06(s, 2H), 2.57–2.52(m, 1H), 2.29–2.11(m, 1H), 2.11 |

TABLE-continued

| Ex. | Y | Stereo | Mol Wt | Mass spec | 1H NMR peaks (CD₃OD) |
|---|---|---|---|---|---|
| | | | | | (d, J=1.3Hz, 3H), 1.80 (s, 3H). |
| 2 | phenylmethyl | E and Z | 600.63 | 601.1 | δ=7.36–7.24(m, 6H), 7.09(d, J=2.3Hz, 1H), 6.91(d, J.3Hz, 1H), 6.83(d, J=8.5Hz, 1H), 5.84–5.83(m, 1H), 5.07 (s, 2H), 2.56–2.52(m, 1H), 2.29–2.24(m, 1H), 2.11(s, 3H), 1.78(s, 3H) |
| 3 | (benzodioxole-methyl) | E and Z | 644.64 | 645.2 | δ=7.24 (br s, 1 H), 7.09 )d, J=8.3Hz, 1H), 6.90 (br s, 1H), 6.86–6.73(m, 4H), 5.91(s, 2H), 5.90–5.82(m, 1H), 4.96(s, 2H), 2.6–2.5(m, 1H)2.3–2.2(m, 1H), 2.11(s, 1H), 1.77(s, 1H). |
| 4 | 3-(fluorophenyl)methyl | E | 618.62 | 619.2 | δ=7.29–6.78(6m, 8H), 5.81–5.80(m, 1H), 5.06 (s, 2H), 2.55–2.49(m, 1H), 2.32–1.92(m, 1H), 2.09(d, J=1.4Hz, 3H), 1.78(s, 3H). |
| 5 | (chromanyl) | E and Z | 642.67 | 643.2 | δ=7.28–7.11(m, 4H), 6.91–6.75(m, 4H), 5.87(br d, J=3.9 Hz, 1H), 5.14–5.08(m, 1H), 2.63–2.58(m, 1H), 2.36–2.25(m, 3H), 2.11(d, J=1.2Hz, 3H), 2.80–2.00(m, 2H). |
| 6 | 5-benzofuranylmethyl | E and Z | 640.65 | 641.2 | δ=7.52–7.39(2m, 2H), 7.25–7.14(m, 3H), 7.06 (d, J=8.3Hz, 1H), 6.8 (s, 1H), 6.80–7.73 (m, 2H), 5.81–5.80(m, 1H), 5.14(s, 2H), 2.55–2.50 (m, 1H), 2.64–2.18(m, 1H), 2.09(s, 3H), 1.77 (s, 3H). |
| 7 | (3-fluoro-4-methoxyphenyl)methyl | E and Z | 648.65 | 649.2 | δ=7.24(br s, 1H), 7.08–6.98(m, 4H), 6.91 (d, J=2.0Hz, 1H), 6.84–6.82(m, 1H), 5.84–5.82(m, 1 H), 4.99(s, 2H), 2.57–2.51(m, 1H), 2.29–2.24(m, 1H), 2.11 |

TABLE-continued

| Ex. | Y | Stereo | Mol Wt | Mass spec | 1H NMR peaks (CD₃OD) |
|---|---|---|---|---|---|
| | | | | | (d, J=1.5 Hz, 3H), 1.78 (s, 3H). |
| 8 | (2,3-dihydro-1,4-benzodioxin-6-yl)methyl | E and Z | 658.67 | 659.2 | δ=7.24(br s, 1H), 7.09 (d, J=8.5Hz, 1H), 6.90 (d, J=1.8Hz, 1H), 6.84–6.73(m, 4H), 5.84–5.83(m, 1H), 4.94(s, 2H), 2.57–2.53(m, 1H), 2.29–2.15(m, 1H), 2.11 (s, 3H), 1.76(s, 3H). |
| 9 | (2,4-dimethoxy phenyl)methyl | E | 660.7 | 661.2 | δ=7.22(br s, 1H). 7.07–7.16(m, 2H), 6.88 (d, J=2.3Hz, 1H), 6.81(dd, J=8.3 and 2.1 Hz, 1H), 6.41–5.47(m, 2H) 5.82(dd, j5.2 and 1.6Hz, 1H), 2.50–2.60 (m, 1H), 2.21–2.28(m, 1 H), 2.09(d, J=1.3Hz, 3H), 1.73(s, 3H). |
| 10 | 2″-deoxy-hygromycin A | E | 495.49 | 496.2 | δ=7.22 (br s, 1H), 7.16 (d, J=8.5Hz, 1H), 6.89 (d, J=2.1Hz, 1H), 6.84 (dd, J=8.3 and 2.1Hz, 1H), 5.89(dd, J=5.2 and 2.3Hz, 1H), 2.44–2.50(m, 1H), 2.22–2.28 (m, 1H), 2.11(s, 3H), 2.09(d, J=1.5 Hz, 3H) |
| 11 | (3-fluorophenyl)ethyl | E | 632.65 | 633.2 | δ=7.24–7.31(m, 2H), 6.81–7.11(m, 6H), 5.80–5.83(m, 1H), 5.19–5.26 (m, 2H), 2.46–2.53(m, 1H), 2.20–2.62(m, 1H), 2.12 (s, 3H), 1.83(s, 3H), 1.46–1.49(m, 3H). |
| 13 | (4-phenylthiazyl)methyl | E | 683 | 684.2 | δ=7.85–7.89(m, 2H), 7.74 (s, 1H), 7.41–7.37 (m, 2H), 7.28–7.32(m, 1H), 7.23(br s, 1H), 7.10(d, J=8.3Hz, 1H), 6.90(d, 1.9Hz, 1H), 6.82(dd, J=8.5 and 1.9Hz, 1H), 5.39(m, 2H), 5.03(s, 2H), 2.55–2.60(m, 1H), 2.23–2.29 (m, 1H), 2.10(s, 3H), 1.86 |
| 14 | (2,4-difluorophenyl)ethyl | E | 650.64 | 651.0 | δ=7.27–7.38(m, 1H) 7.22(br s, 1H), 7.07 (dd, J=12.2 and 8.5 Hz, 1H), 6.79–6.88(m, |

TABLE-continued

| Ex. | Y | Stereo | Mol Wt | Mass spec | 1H NMR peaks (CD$_3$OD) |
|---|---|---|---|---|---|
| | | | | | 4H) 5.81–5.77(m, 1H), 5.27–5.46(m, 1H), 2.43–2.50(m, 1H), 2.16–2.23 (m, 1H), 2.09(s, 3H), 1.80(2s, 3H), 1.45–1.47 (m, 3H). |
| 15 | (3,4-difluorophenyl)ethyl | E | 650.64 | 651.1 | δ=7.24 (br s, 1H), 7.06–7.19(m, 4H), 6.90 (d, J=1.9Hz, 1H) 6.81–6.84(m, 1H), 5.79–5.83(m, 1H), 5.18–5.22 (m, 2H), 2.45–2.53(m, 1H), 2.18–2.26(m, 1H), 2.12(s, 3H), 1.82(2s, 3H), 1.45–1.48(m, 3H). |
| 16 | 1-(2,4-difluorophenyl)propyl | E | 664.66 | 665.0 | δ=7.25–7.29(m, 1H) 7.22(br s, 1H), 7.06(dd, J=14.8 and 8.3Hz, 1H), 6.78–6.88(m, 4H), 5.76–5.80(m, 1H), 5.24–5.30(m, 1H), 2.42–2.49 (m, 1H), 2.16–2.23(m, 1H), 2.10(d, J=1.2Hz, 3H), 1.81(2s, 3H), 1.70–1.92(m, 2H), 0.85–0.91(m, 3H). |
| 17 | (3,5-difluorophenyl)ethyl | E | 650.64 | 651.1 | δ =7.22(br s, 1H), 7.04–7.07(m, 1H), 6.74–6.88(m, 5H) 5.76–5.81 (m, 1H), 5.17–5.21(m, 2H), 2.44–2.53(m, 1H), 2.16–2.24(m, 1H), 2.08 (d, J=1.4Hz, 3H), 1.82 (2s, 3H), 1.43–1.45(m, 3H). |
| 18 | (3-chloro-2,6-difluorophenyl)ethyl | E | 685.08 | 684.9, 687.0 | δ=7.31–7.39(m, 1H) 7.24(br s, 1H),7.02–7.06(m, 1H), 6.79–6.94 (m, 4H), 5.74–5.79(m, 1H), 5.58–5.66(m, 1H), 2.40–2.49(m, 1H), 2.18–2.24(m, 1H), 2.11(s, 3H), 1.79(s, 3H), 1.59 (d, J=6.8Hz, 3H). |
| 19 | (3,4-difluorophenyl)methyl | E | 636.6 | 635.0 | δ=7.08–7.24(m, 5H), 6.90(d, J=2.0Hz, 1H), 5.83–5.85(m, 1H), 5.04 (br s, 1H)2.51–2.56(m, 1H), 2.22–2.29(m, 1H), 2.11(d, J=1.4Hz, 3H), 1.80(s, 3H). |
| 20 | (3,5-difluorophenyl)methyl | E | 636.6 | 636.9 | δ=7.23(br s, 1H), 7.09 (d, J=8.3Hz, 1H), 6.90–6.94(m, 3H), 6.78–6.84(m, 2H), 5.83(dd, J=5.2 and 1.8Hz, 1H), 2.52–2.57(m, 1H), |

TABLE-continued

| Ex. | Y | Stereo | Mol Wt | Mass spec | 1H NMR peaks (CD₃OD) |
|---|---|---|---|---|---|
| | | | | | 5.07(s, 2H), 2.24–2.29 (m, 1H), 2.11(d, J=1.3 Hz, 3H), 1.82(s, 3H) |
| 21 | (2,4-difluorophenyl)methyl | E | 636.6 | 636.9 | δ=7.37–7.43(m, 1H), 7.22(br s, 1H), 7.07(d, J=8.3Hz, 1H), 6.86–6.91(m, 3H), 6.81(dd, J=8.7 and 2.3 Hz, 1H), 5.81–5.83(m, 1H), 5.08 (br s, 2H), 2.40–2.54(m, 1H) 2.20–2.27(m, 1H), 2.09(d, J=1.4 Hz, 3H), 1.75(s, 3H). |
| 22 | (3-chloro-2,6-difluorophenyl)methyl | E | 671.05 | 670.9, 673.0 | δ=7.38–7.44(m, 1H), 7.21(s, 1H), 7.03(d, J=8.3Hz, 1H), 6.92–6.97 (m, 1H), 6.87(d, J=2.1Hz, 1H), 6.78(dd, J=8.5 and 1.8Hz, 1H), 5.80(dd, J=5.3 and 1.8Hz, 1H), 5.13(m, 2H), 2.48–2.53(m, 1H), 2.19–2.26(m, 1H), (d, J=1.5Hz, 3H), 1.70(s, 3H). |
| 23 | 3-chlorophenyl | E | 621.04 | 620.9, 622.2 | δ=7.14–7.24(m, 4H), 7.01–7.08(m,1H), 6.92–6.97(m, 1H), 6.90(d, J =1.9 Hz, 1H), 6.84(dd, J=8.3 and 1.7Hz, 1H), 5.92(d, J=4.5Hz, 1H), 2.62–2.68(m, 1H), 2.28–2.35(m, 1H), 2.11(d, J =1.1Hz, 3H), 1.97(s, 3H). |
| 24 | 3-fluorophenyl | E | 604.59 | 605.0 | δ=7.13–7.26(m, 3H), 6.83–6.95(m, 4H), 6.67–6.71(m, 1H), 5.92(d, J =5.0Hz, 1H), 2.63–2.68 (m, 1H), 2.30–2.35(m, 1H), 2.11(s, 3H), 1.96 (s, 3H). |
| 25 | 3,5-chlorophenyl | E | 655.49 | 654.9 657.0, 659.0 | δ=7.11–7.21(m, 4H), 6.99–7.01(m, 1H), 6.81–6.89(m, 1H), 5.89–5.91(m,1H), 2.61–2.66 (m, 1H), 2.27–2.34(m, 1H), 2.09(d, J=1.4Hz, 3H), 1.95(s, 3H). |
| 26 | (3,5-dichlorophenyl)methyl | E | 669.51 | 668.9, 670.8, 672.0 | δ=7.24–7.32(m, 4H), 7.08(d, J=8.3Hz, 1H), 6.90(d, J=1.7Hz, 1H), 6.83(d, J=8.5Hz, 1H), 5.83(d, J=5.2Hz, 1H), 2.51–2.56(m, 1H), 5.05 (s, 2H), 2.22–2.29(m, |

TABLE-continued

| Ex. | Y | Stereo | Mol Wt | Mass spec | 1H NMR peaks (CD₃OD) |
|---|---|---|---|---|---|
| 27 | (3-chloro-4-fluorophenyl)methyl | E | 653.06 | 652.9, 655.1 | 1H), 2.11(S, 3H), 1.82 (s, 3H).<br>δ=7.41(dd J=7.3 and 5.2Hz, 1H), 7.24–7.26 (m, 1H), 7.22(d, J=1.3 Hz, 1H), 7.14(dd, J= 8.5 and 7.1Hz, 1H), 7.06(d, J=8.3Hz, 1H), 6.88(d, 1.9Hz, 1H), 6.79–6.82(m, 1H), 5.80 (m, 1H), 5.02(s, 2H), 2.48–2.5(m, 1H), 2.24–2.25(m, 1H), 2.09(d, |
| 28 | (3,4-dichlorophenyl)methyl | E | 669.51 | 668.9, 670.9, 672.1 | δ=7.44(d, J=1.8Hz, 1H), 7.41(d, J=8.3Hz, 1H), 7.20–7.23(m, 2H), 7.06(d, J=1.7Hz, 1H), 6.88(d, J=2.1Hz, 1H), 6.80(dd, J=8.7 and 1.8Hz, 1H), 5.81(dd, J =5.2 and 1.7Hz, 1H), 5.03(s, 2H), 2.48–2.54 (m, 1H), 2.20–2.27(m, 1H), 2.09(d, J=1.5Hz, 1H), 1.78(s, 3H). |
| 29 | (3-chloro-5-fluorophenyl)methyl | E | 653.06 | 653.0, 655. 0 | δ=7.21(br s, 1H), 7.15 (br s, 1H), 7.04–7.08 (m, 2H), 7.00(br d, 1H), 6.88(d, J=1.8Hz, 1H), 6.81(dd, J=8.6 and 1.8Hz, 1H), 5.81(dd, J =5.2 and 1.8Hz, 1H), 5.05(s, 2H), 2.49–2.55 (m, 1H), 2.09–2.27(m, 1H), 2.09(d, J=1.4Hz, 3H), 1.80(s, 3H). |
| 30 | (4-chloro-5-fluorophenyl)methyl | E | 653.06 | 653.0, 654.9 | δ=7.36(dd, J=8.1 and 7.6Hz, 1H), 7.22 (br s, 1H), 7.16(dd, J= 10.0 and 2.0Hz, 1H), 7.08(br d, 1H), 7.05(d, J=10.5Hz, 1H), 6.88 (d, J=1.8Hz, 1H), 6.80(dd, J=8.6 and 1.9 Hz, 1H), 5.81(dd, 1.7 and 5.2Hz, 1H), 5.03 (s, 2H 2.20–2.27(m, 1H). |

The synthetic procedures described below may also be useful in preparing the compounds of the present invention.

Preparation of Miscellaneous Alcohol Starting Materials Used in Synthesis of Hydroxylamines Alcohol starting materials may be obtained by reduction of more highly oxidized commercially available compounds. 4-Cyclohexyl benzoic acid may be reduced with lithium aluminum hydride (2.3 equivalents) in tetrahydrofuran to provide the corresponding alcohol. 3-(4-Chlorophenyl)propionic acid may be reduced to the corresponding alcohol using diborane (1.1 equivalents) in tetrahydrofuran at 0° C. to room temperature for 5 hours.

3-Trifluoromethoxybenzaldehyde, 3-cyanobenzaldehyde, benzofuran-2-carboxaldehyde, 1,4-benzodioxan-6-carboxaldehyde, and 3-fluoro-4-methoxybenzaldehyde may be reduced to the alcohol derivatives using sodium borohydride in tetrahydrofuran.

Magnesium sulfate (4 equivalents) in methylene chloride may be treated with concentrated sulfuric acid (1 equivalent), followed by 4-chloromethylbenzoic acid (1 equivalent) and tert-butanol (5.1 equivalents). Stirring overnight at room temperature provides the tert-butyl ester.

4-Amino-3,5-dichlorobenzoic acid may be N-acetylated by treatment with acetyl chloride (1.2 equivalents) in dimethylformamide at 90° C. for 4 hours. The cooled reaction mixture may be poured into cold water, chilled and filtered to provide the acetamide derivative. Reduction of the carboxylic acid was effected with lithium aluminum hydride (2 equivalents) in tetrahydrofuran at 0° C. for 2 hours, provides N-(2,6-dichloro-4-hydroxymethylphenyl)acetamide.

The amino groups of 3-amino-benzyl alcohol and 4-aminomethyl-benzyl alcohol may be protected as the N-tert-BOC derivatives by treatment with di-tert-butyl dicarbonate (1.1 equivalent) in tetrahydrofuran (THF) at reflux until the starting amino compound is consumed.

Reaction of ethyl 4-fluorobenzoate with piperidine (3 equivalents) in acetonitrile may be carried out at reflux for 4 days. Dilution of the cooled reaction mixture with several volumes of water provides a precipitate, which may be filtered to provide ethyl 4-(piperidin-1-yl)benzoate. Reduction of the ester with lithium aluminum hydride (2 equivalents) in tetrahydrofuran provides the corresponding alcohol.

5-Hydroxymethylbenzofuran may be prepared according to the procedure of K. Hiroya, K. Hashimura and K. Ogasawara, Heterocycles (1994) 38, 2463.

2-Phenylpyrimidine-5-carboxaldehyde may be prepared according to the procedure of J. T. Gupton, J. E. Gall, S. W. Riesinger et al., J. Heterocyclic Chemistry (1991) 28, 1281. The aldehyde may be reduced to the corresponding alcohol using sodium borohydride in methanol.

Other methods that may be followed to prepare the various compounds of the present invention are described in the united states provisional patent application entitled "Hygromycin A Derivatives", No. 60/084,058 referred to above.

What is claimed is:
1. A compound of the formula

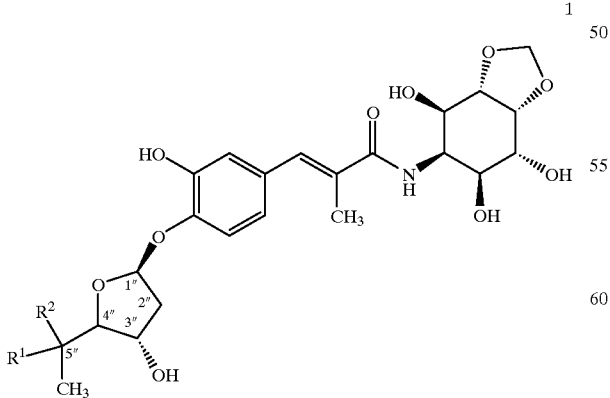

or a pharmaceutically acceptable salt, prodrug, or hydrate thereof wherein:

$R^1$ is H and $R^2$ is —$NR^3R^4$, —$NR^4C(O)R^3$, —$OC(O)NR^3R^4$ or —$OR^3$;

or $R^1$ and $R^2$ are taken together to form =O, =N—$OR^3$, =$CR^4R^3$, =$CR^4C(O)R^3$, =$CR^4C(O)OR^3$, or =$CR^4C(O)NR^3R^4$;

each $R^3$ is independently selected from H, $C_1$–$C_{10}$ alkyl, $C_2$–$C_{10}$ alkenyl, —$(CH_2)_t(C_3$–$C_{10}$ cycloalkyl), —$(CH_2)_t(C_6$–$C_{10}$ aryl), and —$(CH_2)_t$(4–10 membered heterocyclic), wherein t is an integer ranging from 0 to 5, said alkyl group optionally has 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^3$ groups are optionally fused to a benzene ring, a $C_5$–$C_8$ saturated cyclic group, or a 4–10 membered heterocyclic group; the —$(CH_2)_t$— moieties of the foregoing $R^3$ groups optionally have a carbon-carbon double or triple bond where t is an integer between 2 and 5; and the foregoing $R^3$ groups, except H but having any optional fused rings referred to above, are optionally substituted by 1 to 5 $R^5$ groups;

each $R^4$ is independently H or $C_1$–$C_{10}$ alkyl;

each $R^5$ is independently selected from $C_1$–$C_{10}$ alkyl, $C_3$–$C_{10}$ cycloalkyl, halo, cyano, nitro, trifluoromethyl, trifluoromethoxy, azido, —$OR^6$, —$C(O)R^6$, —$C(O)OR^6$, —$NR^7C(O)OR^9$, —$OC(O)R^6$, —$NR^7SO_2R^9$, —$SO_2NR^6R^7$, —$NR^7C(O)R^6$, —$C(O)NR^6R^7$, —$NR^6R^7$, —$S(O)_j(CH_2)_m(C_6$–$C_{10}$ aryl), —$S(O)_j(C_1$–$C_6$ alkyl), wherein j is an integer ranging from 0 to 2, —$(CH_2)_m(C_6$–$C_{10}$ aryl), —$O(CH_2)_m(C_6$–$C_{10}$ aryl), —$NR^7(CH_2)_m(C_6$–$C_{10}$ aryl), and —$(CH_2)_m$(4–10 membered heterocyclic), wherein m is an integer ranging from 0 to 4; said alkyl group optionally has 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^5$ groups are optionally fused to a $C_6$–$C_{10}$ aryl group, a $C_5$–$C_8$ saturated cyclic group, or a 4–10 membered heterocyclic group; and said alkyl, cycloalkyl, aryl and heterocyclic $R^5$ groups are optionally substituted by 1 to 5 substituents independently selected from halo, cyano, nitro, trifluoromethyl, difluoromethoxy, trifluoromethoxy, azido, —$NR^7SO_2R^9$, —$SO_2NR^6R^7$, —$C(O)R^6$, —$C(O)OR^6$, —$OC(O)R^6$, —$NR^7C(O)OR^9$, —$NR^7C(O)R^6$, —$C(O)NR^6R^7$, —$NR^6R^7$, —$OR^6$, $C_1$–$C_{10}$ alkyl, —$(CH_2)_m(C_6$–$C_{10}$ aryl), and —$(CH_2)_m$(4–10 membered heterocyclic), wherein m is an integer ranging from 0 to 4;

each $R^6$ is independently selected from H, $C_1$–$C_{10}$ alkyl, $C_3$–$C_{10}$ cycloalkyl, —$(CH_2)_m(C_6$–$C_{10}$ aryl), and —$(CH_2)_m$(4–10 membered heterocyclic), wherein m is an integer ranging from 0 to 4; said alkyl group optionally has 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^6$ groups are optionally fused to a $C_6$–$C_{10}$ aryl group, a $C_5$–$C_8$ saturated cyclic group, or a 4–10 membered heterocyclic group; and the foregoing $R^6$ substituents, except H, are optionally substituted by 1 to 5 substituents independently selected from halo, cyano, nitro, trifluoromethyl, difluoromethoxy, trifluoromethoxy, azido, —C(O)R$^7$, —C(O)OR$^7$, —OC(O)R$^7$, —NR$^7$C(O)R$^8$, —C(O)NR$^7$R$^8$, —NR$^7$R$^8$, hydroxy, C$_1$–C$_6$ alkyl, and C$_1$–C$_6$ alkoxy;

each R$^7$ and R$^8$ is independently H or C$_1$–C$_6$ alkyl; and,

R$^9$ is selected from the substituents provided in the definition of R$^6$ except H.

2. A compound according to claim 1 wherein R$^1$ and R$^2$ are taken together to form =N—OR$^3$, and R$^3$ is C$_1$–C$_4$ alkyl, C$_2$–C$_4$ alkenyl, —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, having said optionally fused moieties, are optionally substituted by 1 to 5 substituents independently selected from nitro, halo, C$_1$–C$_3$ alkoxy, C$_1$–C$_4$ alkyl, trifluoromethyl, acetamido, tert-butoxycarbonylamino, teft-butoxycarbonylaminomethyl, tert-butoxycarbonyl, —NR$^6$R$^7$, phenyl, cyclohexyl, carboxy, aminomethyl, difluoromethoxy, trifluoromethoxy, cyano, piperidinyl, morpholino, phenoxy, and phenylthio.

3. A compound according to claim 1 wherein R$^1$ and R$^2$ are taken together to form =N—OR$^3$, and R$^3$ is —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, having said optionally fused moieties, are optionally substituted by 1 to 5 substituents independently selected from nitro, halo, C$_1$–C$_3$ alkoxy, C$_1$–C$_4$ alkyl, trifluoromethyl, acetamido, tert-butoxycarbonyl, tert-butoxycarbonylamino, —NR$^6$R$^7$, phenyl, cyclohexyl, carboxy, tert-butoxycarbonylaminomethyl, aminomethyl, difluoromethoxy, trifluoromethoxy, cyano, piperidinyl, morpholino, phenoxy, and phenylthio.

4. A compound according to claim 1 wherein R$^1$ is H, R$^2$ is —NR$^3$R$^4$, R$^4$ is H or methyl, and R$^3$ is —(CH$_2$)$_t$(C$_6$–C$_{10}$ aryl) or —(CH$_2$)$_t$(4–10 membered heterocyclic), wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

5. A compound according to claim 1 wherein R$^1$ is H, R$^2$ is —NR$^4$C(O)R$^3$, R$^4$ is H, and R$^3$ is C$_3$–C$_6$ cycloalkyl, —(CH$_2$)$_t$(C$_6$–C$_{10}$ aryl) or —(CH$_2$)$_t$(4–10 membered heterocyclic), wherein t is an integer ranging from 0 to 2, the aryl group is optionally fused to a 5 or 6 membered heterocyclic group, the heterocyclic group is optionally fused to a benzene ring, and the foregoing R$^3$ groups, having said optionally fused moieties, are optionally substituted by 1 to 5 substituents independently selected from halo, C$_1$–C$_3$ alkoxy, C$_1$–C$_4$ alkyl, and trifluoromethyl.

6. A compound according to claim 1 wherein R$^1$ and R$^2$ are taken together to form =CR$^4$C(O)OR$^3$ or =CR$^4$C(O)NR$^3$R$^4$, R$^4$ is H, and R$^3$ is H, C$_1$–C$_6$ alkyl, C$_3$–C$_6$ cycloalkyl, —(CH$_2$)$_t$(4–10 membered heterocyclic), or —(CH$_2$)$_t$(C$_6$–C$_{10}$ aryl) wherein t is an integer ranging from 0 to 2, the aryl group is optionally fused to a 5 or 6 membered heterocyclic group, the heterocyclic group is optionally fused to a benzene ring, and the foregoing R$^3$ groups, except H but having said optionally fused moieties, are optionally substituted by 1 to 5 substituents independently selected from halo, C$_1$–C$_3$ alkoxy, C$_1$–C$_4$ alkyl, —NR$^6$R$^7$ and trifluoromethyl.

7. A compound according to claim 1 wherein R$^1$ is H, R$^2$ is —OR$^3$, and R$^3$ is C$_1$–C$_4$ alkyl, —(CH$_2$)$_t$(4–10 membered heterocyclic), or —(CH$_2$)$_t$(C$_6$–C$_{10}$ aryl) wherein t is an integer ranging from 1 to 2, the aryl group is optionally fused to a 5 or 6 membered heterocyclic group, the heterocyclic group is optionally fused to a benzene ring, and the foregoing R$^3$ groups, having said optionally fused moieties, are optionally substituted by 1 to 5 substituents independently selected from halo, C$_1$–C$_3$ alkoxy, C$_1$–C$_4$ alkyl, cyclohexyl, cyano, trifluoromethyl, benzyloxy and trifluoromethyl.

8. A compound according to claim 1 wherein R$^1$ is H, R$^2$ is —OC(O)NR$^3$R$^4$, R$^4$ is H, and R$^3$ is —(CH$_2$)$_t$(C$_6$–C$_{10}$ aryl) wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

9. A compound according to claim 1 wherein said compound is selected from the group consisting of:

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-phenylmethyloxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-phenylmethyloxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-pyridinyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-(4-morpholinyl)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[cyclohexylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-dichlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(furan-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-cyclohexylphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-aminophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[[(4-aminomethyl)phenyl]methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[3-(4-chlorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(4-chlorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-(trifluoromethoxy)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-(1-piperidinyl)phenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-fluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[2-(phenylthio)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-phenylpyrimidin-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluoro-4-methoxyphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dihydro-2H-1-benzopyran-4-yl)methyl]oxime;

5-Deoxy-5-[[3-[4-[(5,6-dideoxy-5-(methyl(phenylmethyl)amino-a-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(5,6-dideoxy-5-phenylamino-a-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-5-O-[(3,4-dichlorophenyl)methyl]-β-D-ribo-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-2-yl)methyl]oxime;

5-Deoxy-5-[[3-[4-[(5-methyl-β-D-erythro-hept-5-(E)-enofuranuron-1-ylic acid)oxy]-3-hydroxyphenyl]-2-methyl-1-oxo-2-(E)-propenyl]amino]-1,2-O-methylene-D-neo-inositol, ethyl ester;

5-Deoxy-5-[[3-[4-[[N-(furan-2-yl)methyl]-(5-methyl-β-D-erythro-hept-5-(E)-enofuranuron-1-yl-amide)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(phenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(2-propen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-

(E)-propenyl]amino]-1,2-O-methylene-D-neo-inositol, (E)-O-(2-propen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methylphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methoxyphenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-(trifluoromethyl)phenyl)methyl]oxime;

5-Deoxy-5-[[3-[4-[(2,6-dideoxy-5-O-[(4-chlorophenyl)methyl]-β-D-ribo-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[diphenylmethyl]oxime;

5-Deoxy-5-[[3-[4-[(2,6-dideoxy-5-phenylcarbamate-β-D-ribo-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-5-[(3,4-dichlorophenyl)methyl]carbamate-β-D-ribo-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-5-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-2-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-6-yl) methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-1,3-benzodioxol-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-6-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-5-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-chloro-1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-chloro-1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-fluoro-1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-fluoro-1,2,3,4-tetrahydronaphthalen-1-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-chloro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-chloro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-chloro-3,4-dihydro-2H-1-benzopyran-4-yl)oxime;

5-Deoxy-5-[[3-[4-[(2,6-dideoxy-β-D-eythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-chloro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-fluoro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-fluoro-3,4-dihydro-2H-1-benzopyran-4-yl)oxime;

5-Deoxy-5-[[3-[4-[(2,6-dideoxy-β-D-eythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-fluoro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-fluoro-3,4-dihydro-2H-1-benzopyran-4-yl)oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-3-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenylmethyl)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenylmethyl)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenoxy)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenoxy)phenylmethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-Phenylthiaz-2-yl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-Phenylthiaz-2-yl) methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(2,4-difluorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(2,4-difluorophenyl)propyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(2,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(2,4-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3,5-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3,5-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[1-(3-chloro-2,6-difluorophenyl)ethyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3-chloro-2,6-difluorophenyl)ethyl]oxime;

5-Deoxy-5-[[3-[4-[((2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2,6-difluorophenyl)methyl]oxime;

5-Deoxy-5-[[3-[4-[((2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2,6-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlororophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluororophenyl)]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(phenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(phenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1 ,2-O-methylene-D-neo-inositol, (Z)-O-[(2,1,3-benzoxadiazol-5-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,1,3-benzoxadiazol-5-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3,5,6-tetrafluorophenyl)methyl]oxime;

5-Deoxy-5[4-[(2,6-dideoxy-β-D-eythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluorophenyl)methyl]oxime;

5-Deoxy-5[4-[(2,6-dideoxy-β-D-eythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-3-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-3-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluoro-6-methoxyphenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluoro-6-methoxyphenyl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-thiophen-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-thiophen-2-yl)methyl]oxime;

5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-thiophen-2-yl)methyl]oxime; and 5-Deoxy-5[4-[(2,6-dideoxy-β-D-erythro-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

or a pharmaceutically acceptable salt, prodrug and hydrate of said compounds.

10. A pharmaceutical composition for the treatment of a bacterial infection, a protozoal infection, or a disorder caused by a bacterial infection or a protozoal infection, in a mammal, fish, or bird which comprises a therapeutically effective amount of a compound of claim 1 and a pharmaceutically acceptable carrier.

11. A method of treating a bacterial infection, a protozoal infection, or a disorder caused by a bacterial infection or a protozoal infection, in a mammal, fish, or bird which comprises administering to said mammal, fish or bird a therapeutically effective amount of a compound of claim 1.

12. A method of preparing a compound of claim 1 wherein $R^1$ and $R^2$ are taken together to form $=N-OR^3$ which comprises treating a compound of the formula 4

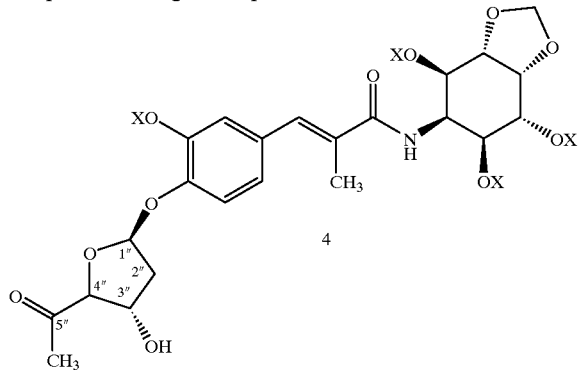

wherein X is a protecting group, with a hydroxylamine of the formula $H_2N-OR^3$, or a salt of said hydroxylamine, where $R^3$ is as defined above, in an inert solvent with the optional addition of base if the salt of the hydroxylamine is used, at a temperature ranging from about 0° C. to 65° C. and subsequent deprotection using a fluoride compound.

13. The method of claim 12 wherein said inert solvent is methanol, ethanol or pyridine, or a mixture of the foregoing solvents, said optional bases is $Na_2CO_3$ or $K_2CO_3$, the temperature range is from 50° C. to 60° C., and said fluoride compound is tetrabutylamonium fluoride or hydrogen fluoride-pyridine compound.

* * * * *